(12) United States Patent
Martelli et al.

(10) Patent No.: US 8,497,466 B2
(45) Date of Patent: Jul. 30, 2013

(54) APPARATUS FOR CHECKING MECHANICAL COMPONENT PARTS WITH OPTICAL DEVICES, AND RELEVANT PROTECTION DEVICE AND METHOD

(75) Inventors: Samuele Martelli, Argelato (IT); Roberto Bruni, Bologna (IT)

(73) Assignee: Marposs, S.p.A., Bentivoglio (IT)

( * ) Notice: Subject to any disclaimer, the term of this patent is extended or adjusted under 35 U.S.C. 154(b) by 344 days.

(21) Appl. No.: 12/676,072

(22) PCT Filed: Sep. 11, 2008

(86) PCT No.: PCT/EP2008/062100
§ 371 (c)(1),
(2), (4) Date: Mar. 2, 2010

(87) PCT Pub. No.: WO2009/034147
PCT Pub. Date: Mar. 19, 2009

(65) Prior Publication Data
US 2010/0206384 A1    Aug. 19, 2010

(30) Foreign Application Priority Data

Sep. 13, 2007 (IT) .............................. BO2007A0623

(51) Int. Cl.
*G02B 7/00* (2006.01)
*B08B 5/02* (2006.01)
*B23Q 11/00* (2006.01)

(52) U.S. Cl.
USPC ....................................... 250/222.1; 359/509

(58) Field of Classification Search
USPC .............. 250/216, 221, 222.1, 239; 359/507, 359/508, 509
See application file for complete search history.

(56) References Cited

U.S. PATENT DOCUMENTS

| | | | | |
|---|---|---|---|---|
| 2,481,808 A | * | 9/1949 | Barna | 405/186 |
| 2,856,542 A | * | 10/1958 | McPheeters | 250/239 |
| 3,321,265 A | * | 5/1967 | Clave et al. | 359/509 |
| 3,565,516 A | * | 2/1971 | Thomas et al. | 359/895 |
| 3,696,230 A | * | 10/1972 | Friedrich | 219/121.75 |
| 3,744,873 A | * | 7/1973 | Jamison | 359/509 |

(Continued)

FOREIGN PATENT DOCUMENTS

| | | |
|---|---|---|
| CN | 1142794 A | 2/1997 |
| DE | 90 17 270 U1 | 3/1991 |

(Continued)

*Primary Examiner* — John Lee
(74) *Attorney, Agent, or Firm* — Dickstein Shapiro LLP

(57) ABSTRACT

An apparatus for checking mechanical component parts, such as tools in machine tools, uses optical devices for emitting and receiving a light beam, for example a laser beam, and sensors for detecting the interruption of such light beam. A protection device for at least one of the optical devices includes pneumatic conduits and a nozzle outputting an air stream from a plurality of holes located around the central conduit through which the light beam passes, so generating a tubular shield which embraces the light beam. The protection device further includes a shutter which can be displaced from a rest position, wherein the central conduit is closed and the inside of the protection device is pressurized, to a working position, wherein the nozzle delivers the air stream in the form of a tubular shield. Passing from the rest position to the working position, the shutter assumes an intermediate transit position in which an air blast is outputted through the central conduit for a short time interval. The shutter has cylindrical surfaces and slides inside a shell of the protection device, driven by plane antirotation surfaces, too.

30 Claims, 4 Drawing Sheets

U.S. PATENT DOCUMENTS

| | | |
|---|---|---|
| 3,749,500 A | 7/1973 | Carlson et al. |
| 3,912,925 A | 10/1975 | Gaskell |
| 4,240,691 A * | 12/1980 | Holmqvist et al. ............ 359/509 |
| 4,413,911 A * | 11/1983 | Rice et al. ..................... 356/438 |
| 4,521,089 A * | 6/1985 | Bohl et al. ..................... 359/507 |
| 4,536,789 A * | 8/1985 | Bains .............................. 348/81 |
| 4,836,689 A * | 6/1989 | O'Brien et al. ................ 374/125 |
| 5,115,342 A * | 5/1992 | Rowe et al. .................... 359/509 |
| 5,146,244 A * | 9/1992 | Myhre et al. ................... 359/509 |
| 5,394,208 A * | 2/1995 | Campbell ...................... 396/429 |
| 5,708,859 A * | 1/1998 | Tajima et al. .................... 396/25 |
| 6,449,526 B1 | 9/2002 | Sachs et al. |
| 6,496,273 B1 * | 12/2002 | Stimpson et al. .............. 356/614 |
| 7,374,294 B2 * | 5/2008 | Willey ........................... 359/507 |
| 7,499,152 B2 | 3/2009 | Roders et al. |
| 7,726,821 B2 * | 6/2010 | Bral ............................... 359/511 |
| 8,096,944 B2 * | 1/2012 | Harrel ............................ 600/157 |
| 2003/0184746 A1 * | 10/2003 | Johnsen et al. ................ 356/300 |
| 2007/0229954 A1 * | 10/2007 | Bral ............................... 359/509 |
| 2008/0285131 A1 * | 11/2008 | O'Kane et al. ................. 359/509 |
| 2008/0285132 A1 * | 11/2008 | O'Kane ......................... 359/509 |
| 2009/0207494 A1 * | 8/2009 | Gelbart et al. ................. 359/509 |
| 2010/0206384 A1 * | 8/2010 | Martelli et al. .................... 137/1 |

FOREIGN PATENT DOCUMENTS

| | | |
|---|---|---|
| DE | 102 27 242 A1 | 2/2004 |
| DE | 103 37 242 A1 | 3/2005 |
| EP | 0 098 930 A2 | 1/1984 |
| EP | 0 985 493 A2 | 3/2000 |
| EP | 1 050 368 A1 | 11/2000 |
| EP | 1 591 196 A1 | 11/2005 |
| FR | 2 343 555 A1 | 10/1977 |
| JP | 2001-328049 A | 11/2001 |
| JP | 2007-268646 A | 10/2007 |
| WO | WO 95/20458 A1 | 8/1995 |

* cited by examiner

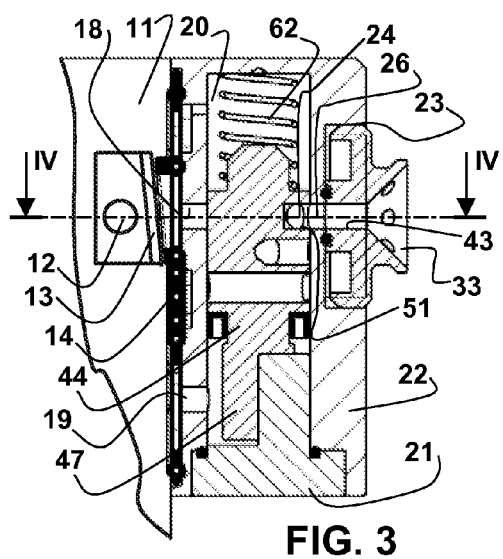
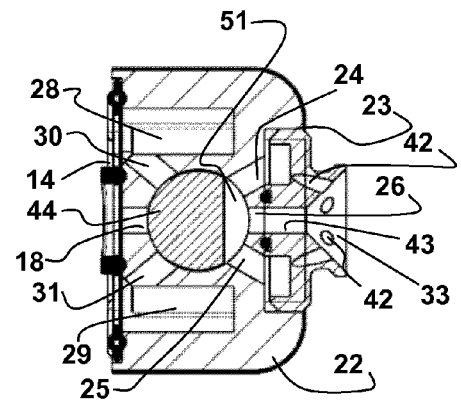
FIG. 3    FIG. 4
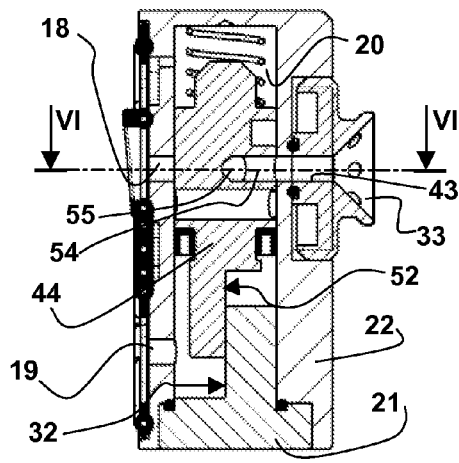
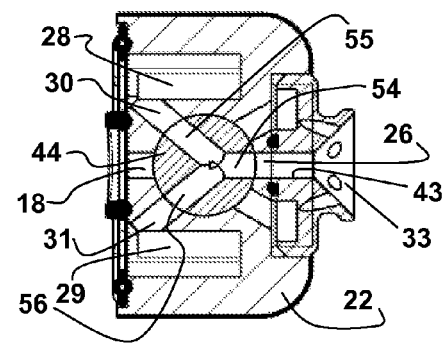
FIG. 5    FIG. 6
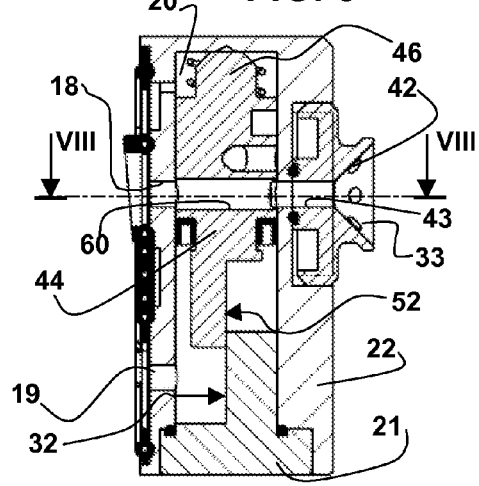
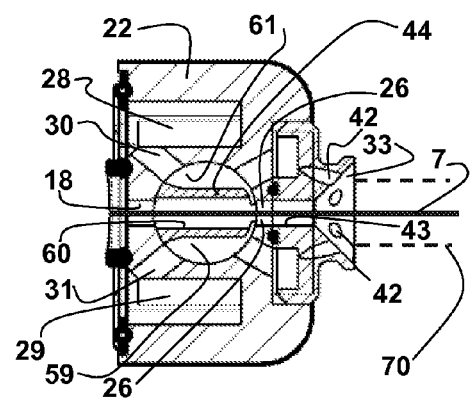
FIG. 7    FIG. 8

APPARATUS FOR CHECKING MECHANICAL COMPONENT PARTS WITH OPTICAL DEVICES, AND RELEVANT PROTECTION DEVICE AND METHOD

TECHNICAL FIELD

The present invention relates to an optoelectronic apparatus for checking dimensions, position or integrity of mechanical component parts, with optical devices, in particular an emitter and a receiver which are aligned along a checking direction and are adapted to emit and receive, respectively, a light beam, a sensor device for detecting the interruption of the light beam, and a protection device for at least one of the optical devices, the protection device including a pneumatic system with a nozzle for outputting a protection gas stream.

The present invention also relates to a method for achieving a protection in an optoelectronic checking apparatus which uses a light beam arranged along a checking direction, the method including the step of delivering a protection gas at an optical device of the apparatus which emits or receives the light beam.

The present invention also relates to a protection device for an optical device adapted to emit or receive a light beam, including a pneumatic system with a nozzle for outputting a protection gas stream.

BACKGROUND ART

There are known apparatuses and methods using light rays or beams for checking the dimensions or the presence, the arrangement and possible breakages of mechanical component parts, for example of tools in machine tools.

U.S. Pat. No. 3,912,925 discloses, for example, a drilling machine in which devices for checking the integrity of the tools employ transversal light beams which have limited thickness and are substantially coplanar with respect to the feed direction of the tools. The non-interruption of a light beam at a specific position of the tool is detected, and notifies an anomalous condition of the tool.

U.S. Pat. No. 3,749,500 shows different applications of optical gauges for checking dimensions (diameters of cylindrical pieces) or wear of tools (FIG. 17). Other checking apparatuses that employ a light beam and detect its interruption are known from other patent documents, such as publications No. FR-A-2343555, EP-A-0098930, EP-A-1050368 and DE-10337242.

In the optical and optoelectronic apparatuses, component parts such as lenses, mirrors, photodiodes, etc., are needed to be protected against dust and other foreign materials. This need is particularly pressing in optoelectronic apparatuses which operate in industrial environments, for example for checking dimensions of pieces with high standards of accuracy.

In the checking apparatuses using a light beam and operating in a workshop environment, the presence of dirt located at the emitter and/or the receiver affects the correct reception of the emitted light beam in a direct and hard way, and thus affects the correct operation of the apparatus. Such a problem is faced and partly solved in different ways. As disclosed in patent No. DE-A-10227242, there can be movable mechanical protections such as shutters that uncover the optical devices only during the time interval in which the checking is carried out. In such a way, in the course of the machining, the optical device is mechanically protected and the propagation conduit of the light beam can not be reached by chips and cooling. There can be also included cleaning nozzles blowing compressed air on the glasses of the casing that house the optical devices, as mentioned and shown for example in patent applications No. EP-A-0098930 and EP-A-1050368. The latter document also shows different solutions, wherein an optical device comprises a mechanical protection screen with a conduit for allowing the light beam in output (in case of the emitter) or in input (in case of the receiver) to pass through, and a pneumatic circuit blowing compressed air outwards from said casing through said conduit for preventing the dirt or other foreign material from penetrating from the conduit and reaching the optical device.

Documents no. U.S. Pat. No. 3,749,500 and DE-A 10337242 also comprise the implementation of pressurized units housing the optical devices.

According to the known solutions disclosed in the documents No. EP-A-1050368 and DE-A-10337242, the compressed air passes through the conduit of the light beam even—and especially—during the checking operations carried out by means of the apparatus. The turbulences in the compressed air stream can negatively affect the correct operation of the apparatus, causing unwanted and uncontrollable reflections and refractions of the light beam which is transmitted and/or received. For the purpose of overcoming, at least partly, such a problem the patent application No. EP-A-1050368 shows conduits being oblique with respect to the light beam direction, so as to minimize the negative influence of the compressed air stream on the correct propagation of the light beam. According to a different embodiment disclosed in the patent application No. DE-A-10337242, a porous "homogenizing" element located inside the protection casing filters the air so causing a laminar flow in the stream aimed to pass through the conduit. This enables to limit vortex and turbulences and thus the negative and uncontrollable effects on the light beam. The "homogenizing" element can be tubular-shaped and can be made of sintered material (metal, plastic, or other material), which is worked in such a way to obtain holes and slots having dimensions of some tens of micron.

Even thought the mentioned disadvantage is limited, both the solutions do not enable to substantially solve the problem: the negative influence on the light beam caused by the air stream, with a necessarily high flow, passing through the same conduit during the checking operations of the apparatus is not completely avoided.

DISCLOSURE OF THE INVENTION

Object of the present invention is to provide an optical checking apparatus using a light beam which ensures high standards of performance and is particularly reliable even in a workshop environment, thus overcoming problems of the known apparatuses, in particular insofar as the protection of optical devices is concerned.

A further object is to provide a method and a device for protecting optical devices in a checking apparatus that employ compressed air, or other gas, and that enable a particular reliability over time during the performances of the apparatus even in a workshop environment.

This and other objects and advantages are achieved by an apparatus according to claim 1, by a method according to claim 11, and by a protection device according to claim 17.

BRIEF DESCRIPTION OF THE DRAWINGS

The invention is now described with reference to the enclosed sheets of drawings, given by way of non limiting examples, wherein:

FIG. 3 is a section of the protection device of FIG. 2 which is shown in a first working condition and is connected to the associated optical device;

FIG. 4 is a transversal section of the protection device of FIG. 3, on the line IV-IV of FIG. 3;

FIG. 5 is a section of the protection device of FIG. 2, in a second working condition;

FIG. 6 is a transversal section of the protection device of FIG. 5, on the line VI-VI of FIG. 5;

FIG. 7 is a section of the protection device of FIG. 2, in a third working condition;

FIG. 8 is a transversal section of the protection device of FIG. 7, on the line VIII-VIII of FIG. 7;

BEST MODE FOR CARRYING OUT THE INVENTION

Figure 1:
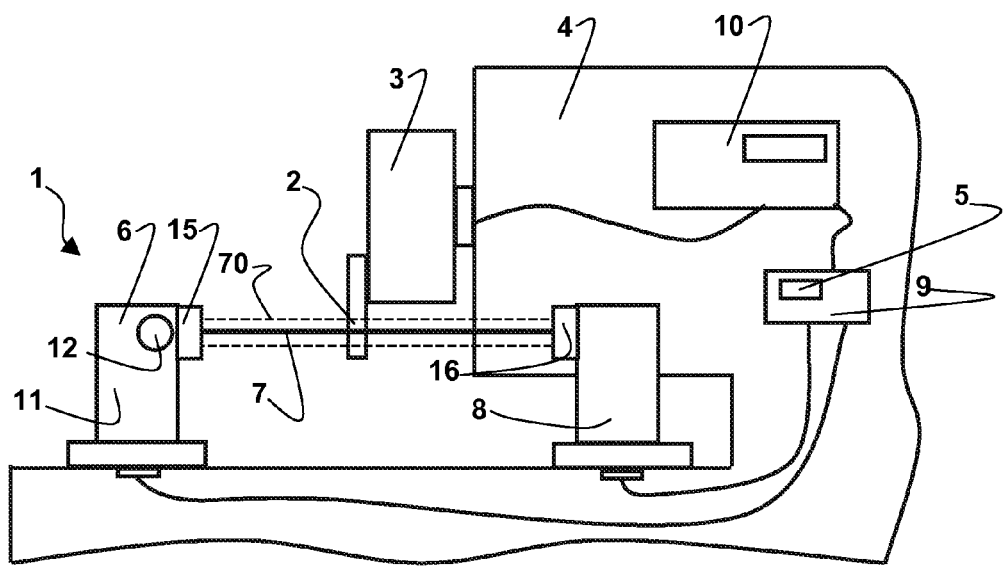
FIG. 1 is a very simplified side view of a checking system including an optoelectronic apparatus according to the present invention.

FIG. 1 shows, in a very simplified way, a checking system with an optoelectronic apparatus 1 according to the present invention during the checking of a mechanical piece 2, in particular a tool arranged in the turret 3 of a lathe 4, whereto the apparatus 1 is coupled.

The apparatus 1 includes optical devices, in particular an emitter 6, i.e. a device for generating and transmitting a light beam 7, for example a laser beam, along a checking direction, and a receiver 8, arranged along said checking direction, which receives the light beam 7. A processing unit 9 is electrically connected to the emitter 6 and to the receiver 8, and includes, among other things, a sensor 5 which detects whether the light beam 7 is received by the receiver 8 or is not received owing to the interruption of the light beam 7. The system includes a checking unit 10, connected to the processing unit 9, which controls the machining movements of the lathe 4 in a know way, by means of suitable activation devices that are known as well, and thus not illustrated in the figure.

Figure 2:
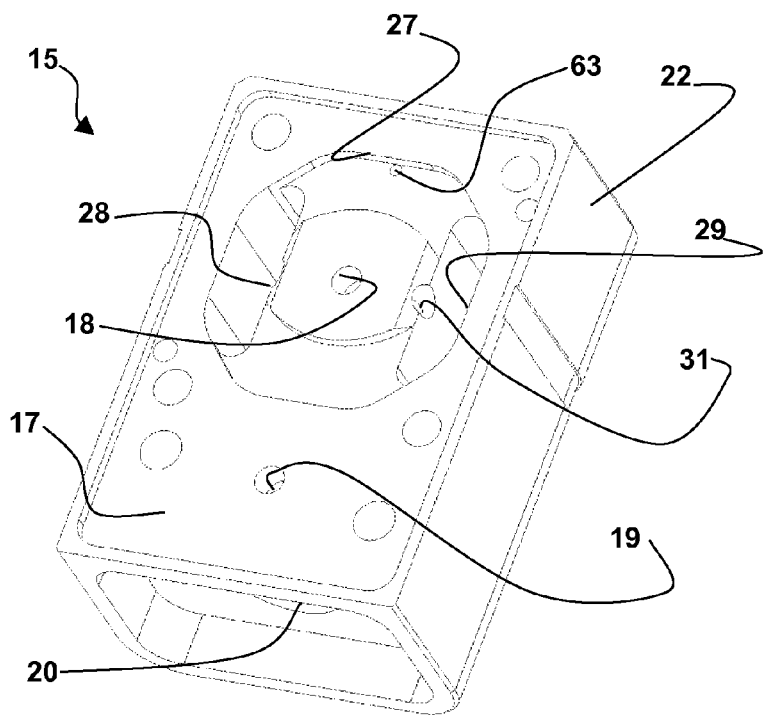
FIG. 2 is a back perspective view of a protection device for an optical device of an apparatus according to the present invention.

The emitter 6 includes a casing 11 which houses, among other things, a light source 12, and a protection device 15, or shutter assembly, which is shown in FIG. 2, and, in different working moments, in FIGS. 3 to 8.

The shutter assembly 15 essentially includes three elements: a support element with a shell 22, a nozzle 33, and a distributor element, or shutter, 44.

The shell 22 is connected to the casing 11 of the emitter 6 at an end wall 17, with a first conduit 18 aligned with the light source 12, in particular communicating with a transparent wall 13, for example a protection glass covering the light source 12. FIG. 3 shows in a simplified way a portion of the casing 11 whereto the protection device 15 is coupled, and also the light beam 12 and the glass 13. A sealing member 14 is placed between the end wall 17 and the casing 11, and includes different sealing profiles, among which an annular profile located at the glass 13. A second conduit 19 in the wall 17 communicates with a longitudinal internal seat 20, substantially cylindrically shaped, of the shell 22. A closing and antirotation element 21—forming a part of the support element and being visible in FIGS. 3, 5, and 7—closes an end of the shell 22 and defines a stationary guide surface 32, substantially plane, for the shutter 44. A seat 23, substantially cylindrically shaped, for the nozzle 33 is arranged facing the first conduit 18. Communication conduits 24, 25, and 26 are placed between the seat 23 and the longitudinal internal seat 20. The conduit 26 is aligned with the first conduit 18 along the checking direction of the apparatus, while the conduits 24 and 25 are divergent with respect to such checking direction. An opening 27 in the wall 17 and internal surfaces of the shell 22 located around the conduit 18 define two recesses 28 and 29 that communicate with the longitudinal internal seat 20 through the associated radial conduits 30 and 31.

Figure 9:
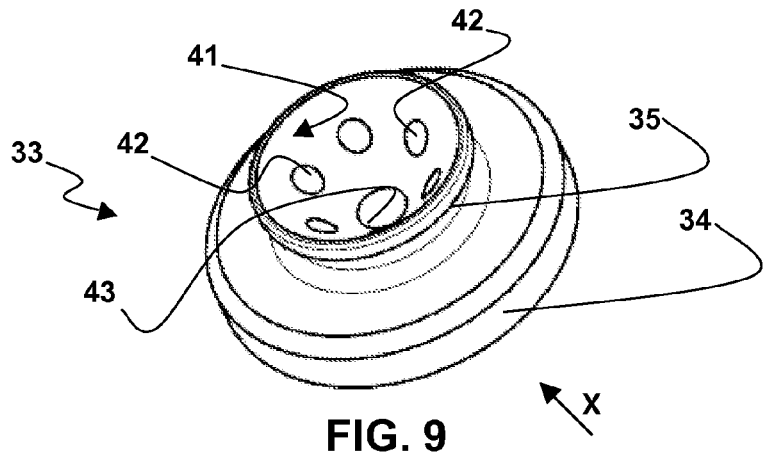
FIG. 9 is an enlarged scale, perspective view of a component part of the protection device of FIGS. 2-8.
Figure 10:
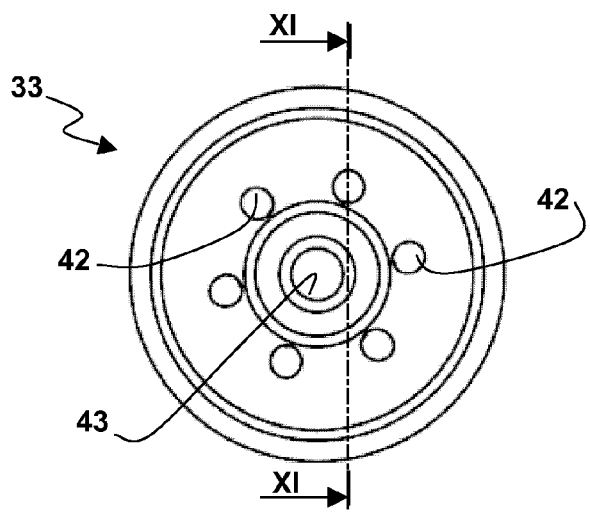
FIG. 10 is a back view of the component part of FIG. 9, along the direction indicated by the arrow X of FIG. 9.
Figure 11:
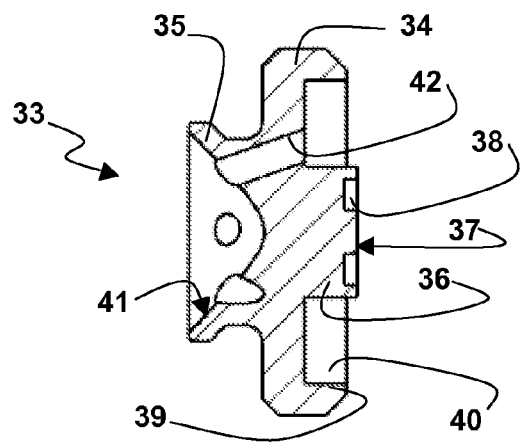
FIG. 11 is a section of the component part of FIGS. 9 and 10 on the line XI-XI of FIG. 10.

The nozzle 33, visible also in FIGS. 9, 10, and 11, is arranged and fixed, for example by interlocking or by means of screws, in the seat 23 of the shell 22, and substantially includes a channelling portion 34 and a delivery portion 35. The channelling portion 34 includes a substantially cylindrical central body 36 having a free end which has a plane surface 37 and an annular slot 38 for housing a sealing gasket ("O-ring"), visible in FIGS. 3 to 8. An opened annular cavity 40 is defined by the central body 36 and by a side 39 of the portion 34. The delivery portion 35 is substantially funnel-shaped and has a hollow drilled surface 41 facing the outside, and a plurality of oblique conduits 42, six in the illustrated example, located between the drilled surface 41 and the annular cavity 40. An axial conduit 43 passes through the nozzle 33 from the plane surface 37 of the central body 36 to the drilled surface 41 and is arranged aligned with the first conduit 18 of the wall 17 along the checking direction.

Figure 12:
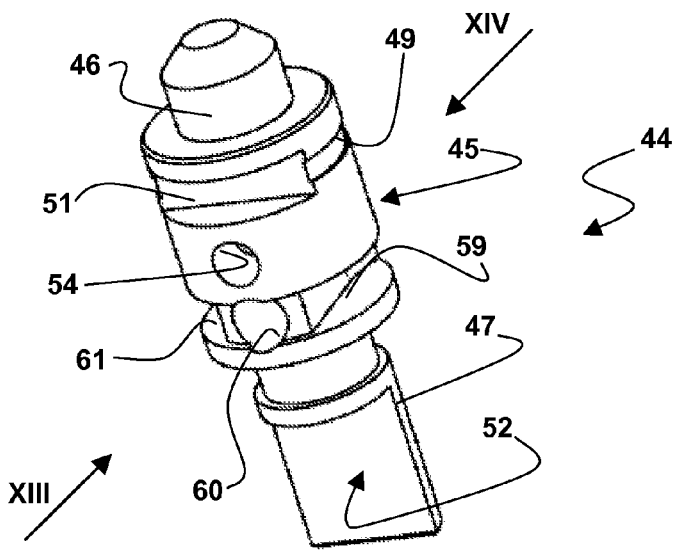
FIG. 12 is an enlarged scale, perspective view of another component part of the protection device of FIGS. 2-8.
Figure 13:
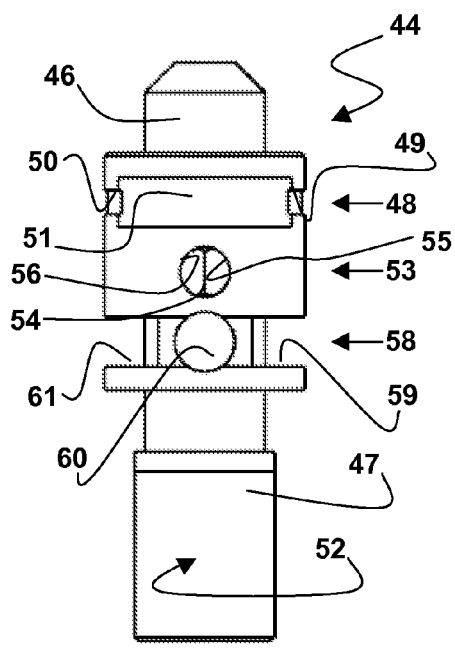
FIG. 13 is a front view of the component part of FIG. 12 along the direction indicated by the arrow XIII of FIG. 12.
Figure 14:
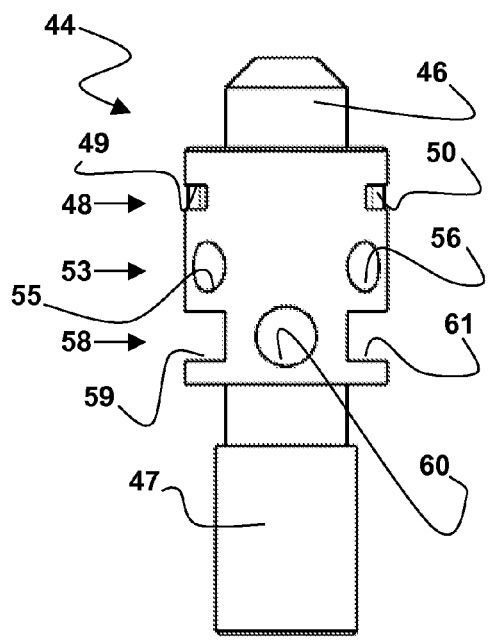
FIG. 14 is a back view of the component part of FIG. 12 along the direction indicated by the arrow XIV of FIG. 12.

The shutter 44, also visible in FIGS. 12, 13, and 14, includes a selective distribution body 45 which is substantially cylindrically shaped and has apertures and recesses, that will be hereinafter described, and abutment end portions 46 and 47. The shutter 44 is arranged in the longitudinal internal seat 20 of the shell 22 wherein the former can slide with reduced clearance between a rest position (FIGS. 3, 4) defined by the longitudinal abutment between surfaces of the abutment end portion 47 and of the closing and antirotation element 21, and a working position (FIGS. 7, 8) defined by the abutment between the abutment end portion 46 and an internal surface of the shell 22. A compression spring 62 is housed in the seat 20 and urges the shutter 44 in the rest position. A transversal guide surface 52 of the portion 47 and the stationary guide surface 32 of the closing and antirotation element 21 mutually cooperate to guide the longitudinal displacements of the shutter 44 in the seat 20 and prevent the shutter 44 from rotating about a longitudinal axis.

The selective distribution body 45 substantially includes three different sections 48, 53, 58, longitudinally separated, that, as it will be hereinafter described, comprise various apertures—in the form of conduits, indentations, recesses, or other aperture types—enabling the selective distribution of the compressed air. The different sections 48, 53, and 58 are alternatively arranged, at different operation moments of the apparatus, aligned with the first conduit 18 and with the axial conduit 43 of the nozzle 33, i.e. with the checking direction, as shown in FIGS. 3 to 8.

The first section 48 has two areas with a reduced diameter 49 and 50 and a transversal notch 51 which is aimed to be arranged transversally to the checking direction. The second section 53 has three radial holes 54, 55, and 56 that are coplanar and in communication with each other. One of such holes, 54, is aimed to be arranged parallel to the checking direction, whereas the other two holes, 55 and 56, are aimed to be arranged along oblique directions convergent with respect to said checking direction. The third section 58 defines a diametral through hole 60—aimed to be arranged parallel to the checking direction—and hollows 59 and 61 defined by two notched areas that are substantially parallel to said checking direction.

Insofar as the protection device, or shutter assembly 15, is concerned, the operation of the apparatus 1 is herein described.

During the machining operations of a piece (not shown in the figures) in the machine tool 4, the shutter 44 is placed in the rest position, which is shown in FIGS. 3 and 4 and is defined by the longitudinal abutment of the abutment portion 47 on the closing and antirotation element 21. In the embodiment illustrated in the figures, the shutter 44 is urged in the rest position by the action of the spring 62, but in normal operating conditions of the apparatus, the spring 62 can be omitted and there can be utilized the pressure applied by the protection gas in the seat 20 at the portion 46, thanks to suitable openings (for example the hole 63 of FIG. 2). The first section 48 of the selective distribution body 45 is placed at the checking direction, and the shutter 44 mechanically closes the first conduit 18, so as to protect the glass 13 of the light source 12 against dirt and foreign material such as chips and cooling located in the workshop environment. Compressed air—or a different type of gas—is conveyed by suitable pneumatic circuits placed in the casing 11 of the emitter 6 into the recesses 28, 29 of the shell 22. This occurs in a substantially continuous way during all the operation phases of the apparatus 1. Through the radial conduits 30 and 31, the narrow spaces defined between the internal wall of the seat 20 and the areas with a reduced diameter 49 and 50, the opening defined by the transversal notch 51 and the communication conduits 24, 25 and 26, the compressed air reaches the nozzle 33, emitting air through all the holes of the surface 41.

This air barrier, which has a very low flow in output from the above described path, is a further protection in addition to the mechanical protection of the shutter 44, and thus prevents build up of dirt or other foreign material on the drilled surface 41 of the nozzle 33 which is located in an exposed position.

When the optoelectronic apparatus 1 has to carry out a checking, the shutter 44 is displaced, for example by means of a distinct pneumatic system which sends compressed air to the longitudinal internal seat 20 of the shell 22 through the second conduit 19. While displacing towards the working position defined by the abutment between the abutment portion 46 and an internal surface of the shell 22 (FIGS. 7 and 8), the second section 53 of the body 45 passes through the area including the checking direction. According to such an embodiment (to which FIGS. 5 and 6 make reference) the compressed air located in the recesses 28 and 29 passes through the body 45 of the shutter 44 in a more direct way through the radial holes 55 and 56 that are arranged aligned with the radial conduits 30 and 31, and the radial hole 54. Through the communication conduit 26, aligned with the hole 54, the air reaches with a high pressure and flow the axial conduit 43 of the nozzle 33 and blows outwards an air blast aimed to remove possible build up of dirt or foreign material occurred along the checking direction in the course of the machining. It should be noted that at this intermediate transit position between the rest position and the working position, the shutter 44 mechanically holds closed the first conduit 18, which communicates with the light source 12. Moreover, the whole amount of air is emitted through the axial conduit 43 and doesn't reach the oblique conduits 42, thus enabling to obtain a blast with a higher flow.

As already stated, at the end of the displacement starting from the rest position, the shutter 44 is located at the working position to which FIGS. 7 and 8 make reference. According to such an embodiment, the diametral through hole 60 is arranged aligned with the first conduit 18, with the communication conduit 26 and with the axial conduit 43 of the nozzle 33 along the checking direction of the apparatus, enabling the light beam 7 emitted by the source 12 to pass through. The compressed air, from the recesses 28 and 29 and the radial conduits 30 and 31, passes through the rather wide spaces defined by the wall of the internal seat 20 of the shell 22 and by the hollows 59 and 61 and reaches the two divergent communication conduits 24 and 25.

Then, the air enters in the opened annular cavity 40 of the nozzle 33 and is blown, with a rather high flow, through the holes of the surface 41 corresponding to the oblique conduits 42. In such a way, the air stream outputted by the oblique conduits 42 provides a tubular protective shield being substantially continuous around the light beam 7, i.e. it takes a substantially cylindrical, or prismatic, hollow shape which protects the laser beam 7 against chips or cooling, by deviating the foreign material from trajectories that could interfere with the checking direction. The broken lines and reference number 70 in FIGS. 1 and 8 represent such a tubular shield in a simplified way. Hence, the protection air with a high flow does not interfere with the light beam 7 and there not occur the problems of the known art due to unwanted and uncontrollable refractions/reflections in the laser beam sharing the path with high flow gas. Moreover, thanks to the sealing member 14, the air never contacts the transparent wall 13 of the light source 12 and the various problems of the known solutions owing to build up of dirt caused by the protection gas is avoided.

According to an optional characteristic which is clearly visible in FIG. 8, the diametral through hole 60 and the surfaces defining the hollows 59 and 61 are shaped in such a way that a little amount of air, with a very reduced flow, can pass through the communication conduit 26 and exit through the axial conduit 43 of the nozzle 33. This enables to obtain a further protective effect for removing possible cooling drops located along the checking direction. By virtue of the very low flow of the air, it is possible to do so without introducing troubles caused by air.

The particular solution herein illustrated for preventing the shutter 44 from rotating about its own axis provides special advantages with respect to known solutions, wherein a radial dowel connected to a stationary part such as the shell 22 cooperates with a longitudinal groove placed in the movable element (for example the shutter 44). The advantages concern both the simplicity of machining and assembling the component parts, and the reliability deriving from this simplicity.

A protection device, or shutter assembly, 16 having the same characteristics as the above described device 15, can be included in the receiver 8, as schematically shown in FIG. 1. In such a way it is possible to implement a tubular shield 70 covering the whole trajectory of the light beam 7.

Alternative embodiments with respect to what has been hereinbefore described and shown in the figures are possible within the scope of the present invention.

The optoelectronic apparatus 1 can use, for example, a light beam 7 differing from a laser beam in a per se way.

Moreover, the shutter 44 can be differently shaped or arranged, and can not include, for instance, the characteristics illustrated with reference to the second section 53 of the body 45, or to the first section 48. An apparatus which has a protection device in which the movable shutter can be omitted and suitable conduits for conveying under pressure gas to the nozzle 33 and for providing a protection stream being substantially similar to the above mentioned tubular shield 70 falls within the scope of the present invention.

The number of holes and the shape of the surface 41 of the nozzle 33 can vary. Both the orientation and the number of the conduits 42 arranged around the axial conduit 43 canH also be different from what is illustrated in the figures.

The invention claimed is:

1. An optoelectronic apparatus for checking dimensions, position or integrity of mechanical component parts, the apparatus comprising:
   optical devices, in particular an emitter and a receiver which are aligned along a checking direction and emit and receive, respectively, a light beam;
   a sensor device for detecting the interruption of the light beam; and
   a protection device for at least one of said optical devices, the protection device including a pneumatic system with a nozzle for outputting a protection gas stream,
   wherein said nozzle includes an axial conduit substantially aligned along said checking direction and a plurality of conduits arranged around the checking direction for providing a gas stream substantially in the form of a tubular cylindrical protective shield around said checking direction that does not interfere with the light beam, and wherein said protective shield extends between the optical devices.

2. The apparatus according to claim 1, wherein the protection device includes a support element carrying said nozzle and comprising an internal seat, and a distributor element which is arranged in said internal seat of the support element and can be displaced from a rest position to a working position.

3. The apparatus according to claim 2, wherein the distributor element defines a substantially plane transversal guide surface, that cooperates with a stationary guide surface integral with the support element.

4. The apparatus according to claim 3, wherein the support element includes a shell defining said internal seat and a closing and antirotation element which defines said stationary guide surface.

5. The apparatus according to claim 2, wherein the distributor element includes a diametral through hole adapted to be arranged substantially along the checking direction at said working position.

6. The apparatus according to claim 5, wherein the distributor element includes hollows for enabling the protection gas to pass through, said hollows being in fluid communication with said plurality of conduits of the nozzle at said working position of the distributor element.

7. The apparatus according to claim 2, wherein the distributor element includes three different sections adapted to be arranged at the checking direction in said rest position, in said working position and in an intermediate transit position.

8. The apparatus according to claim 1, wherein, in the nozzle, the said plurality of conduits are obliquely arranged with respect to the checking direction.

9. The apparatus according to claim 1, wherein said protection gas is compressed air.

10. A method for achieving a protection in an optoelectronic checking apparatus which uses a light beam arranged along a checking direction, the method including the step of:
    delivering a protection gas at an optical device of the apparatus emitting or receiving the light beam,
    wherein said protection gas is delivered along a plurality of directions around said checking direction, so providing a gas stream in the form of a tubular cylindrical protective shield around said light beam that does not interfere with the light beam, and wherein said protective shield extends between the optical device at which it is delivered and the other of the optical devices for emitting or receiving the light beam.

11. The method according to claim 10, wherein the protection gas is delivered along a plurality of conduits of a nozzle, that define said plurality of directions, for providing said gas stream.

12. The method according to claim 10, wherein a distributor element at said optical device is displaced from a rest position to a working position, a conduit, which enables the light beam to pass through, being covered and uncovered by said distributor element at said rest position and working position, respectively.

13. The method according to claim 12, wherein the protection gas is delivered along said plurality of directions at the working position of the distributor element.

14. The method according to claim 12, wherein, at a transit position of the distributor element between said rest position and working position, the protection gas is delivered along an axial conduit which enables the light beam to pass through.

15. The method according to claim 12, wherein, at the rest position of the distributor element, the protection gas is delivered with a low flow.

16. A protection device for an optical device adapted to emit or receive a light beam along a checking direction, including a pneumatic system with a nozzle for outputting a protection gas stream,
    wherein said nozzle includes an axial conduit to be substantially aligned along said checking direction and a plurality of conduits to provide a gas stream substantially in the form of a tubular cylindrical protective shield around said light beam.

17. The protection device according to claim 16, including a support element which carries said nozzle and comprises an internal seat, and a distributor element which is arranged in said internal seat of the support element and can be displaced from a rest position to a working position.

18. The protection device according to claim 17, wherein the distributor element defines a substantially plane transversal guide surface that cooperates with a stationary guide surface which is integral with the support element.

19. The protection device according to claim 18, wherein the support element includes a shell defining said internal seat and a closing and antirotation element defining said stationary guide surface.

20. The protection device according to claim 17, wherein the distributor element includes a diametral through hole, adapted to be arranged substantially along the checking direction at said working position, and hollows for enabling the protection gas to pass through, said hollows being in fluid communication with said plurality of conduits of the nozzle at said working position of the distributor element.

21. The protection device according to claim 17, wherein the distributor element includes a selective distribution body having three different sections adapted to be alternatively arranged at the checking direction in the rest position, in the working position and in an intermediate transit position.

22. The protection device according to claim 21, wherein said selective distribution body includes various apertures at the three different sections enabling the selective distribution of the protection gas to said nozzle in said rest position, said intermediate transit position and said working position of the distributor element.

23. The protection device according to claim 16, wherein the conduits of said plurality are obliquely arranged with respect to the checking direction.

24. The protection device according to claim 16, wherein said protection gas is compressed air.

25. A protection device for an optical device adapted to emit or receive a light beam along a checking direction, including:
   a pneumatic system with a nozzle for outputting a protection gas stream, said nozzle including a plurality of conduits to provide a gas stream substantially in the form of a tubular cylindrical protective shield around said light beam;
   a support element which carries said nozzle and comprises an internal seat; and
   a distributor element which is arranged in said internal seat of the support element and can be displaced from a rest position to a working position, the distributor element including a diametral through hole, adapted to be arranged substantially along the checking direction at said working position, and hollows for enabling the protection gas to pass through, said hollows being in fluid communication with said plurality of conduits of the nozzle at said working position of the distributor element.

26. The protection device according to claim 25, wherein the distributor element includes a selective distribution body having three different sections adapted to be alternatively arranged at the checking direction in the rest position, in the working position and in an intermediate transit position.

27. The protection device according to claim 1, wherein the protective shield extends between the optical devices along an entire trajectory of the light beam.

28. The protection device according to claim 27, comprising a protection device for each of said optical devices.

29. The method according to claim 10, wherein the protective shield extends along an entire trajectory of the light beam.

30. The protection device according to claim 16, wherein the protective shield extends along an entire trajectory of the light beam.

* * * * *